United States Patent [19]

Derouane et al.

[11] Patent Number: 4,695,642

[45] Date of Patent: Sep. 22, 1987

[54] METHOD FOR PREPARING CRYSTALLINE ZIRCONIUM PHOSPHATES

[75] Inventors: E. G. Derouane, Namur, Belgium; R. M. Dessau, Edison, N.J.; I. J. Heilweil, Princeton, N.J.; G. T. Kerr, Lawrenceville, N.J.

[73] Assignee: Mobil Oil Corporation, New York, N.Y.

[21] Appl. No.: 902,121

[22] Filed: Sep. 2, 1986

Related U.S. Application Data

[63] Continuation of Ser. No. 676,968, Nov. 30, 1984, abandoned.

[51] Int. Cl.$^4$ .................................................. C07F 7/00
[52] U.S. Cl. ............................................ 556/14; 546/2; 546/3; 546/6; 544/225; 548/101; 548/102; 548/105; 556/17
[58] Field of Search .................... 556/14, 17; 544/225; 546/2, 3, 6; 548/101, 102, 105

[56] References Cited

U.S. PATENT DOCUMENTS

| | | | |
|---|---|---|---|
| 3,397,215 | 8/1968 | Hettinger, Jr. | 556/1 X |
| 3,503,718 | 3/1970 | Riess et al. | 556/14 X |
| 3,539,605 | 11/1970 | Oberhofer | 556/1 X |
| 4,298,723 | 11/1981 | DiGiacomo et al. | 528/271 |
| 4,310,440 | 1/1982 | Wilson et al. | 252/435 |
| 4,376,709 | 3/1983 | Johnson et al. | 534/11 X |
| 4,454,061 | 6/1984 | Johnson | 534/11 X |

FOREIGN PATENT DOCUMENTS 0159756 10/1985 European Pat. Off. .

Primary Examiner—Helen M. S. Sneed
Attorney, Agent, or Firm—A. J. McKillop; M. G. Gilman; L. P. Hobbes

[57] ABSTRACT

A new crystalline zirconium phosphate composition and method for its synthesis are provided. The composition has ion exchange properties and is readily convertible to catalytically active material by thermal treatment.

42 Claims, No Drawings

METHOD FOR PREPARING CRYSTALLINE ZIRCONIUM PHOSPHATES

This is a continuation of copending application Ser. No. 676,968, filed on Nov. 30, 1984 now abandoned The present invention relates to a method of preparing zirconium phosphates in the presence of a bulky organic cation. The resulting material exhibits thermal stability, ion exchange properties, sorption capacity and distinct X-ray diffraction patterns.

Crystalline zirconium phosophates are known to exhibit a capacity for ion exchange. Alpha zirconium phosphate $Zr(HPO_4)_2 \cdot H_2O$ is known to have a small interlayer radius (7.6 angstroms) which results in slow exchange of cations having a large ionic radius such as $Cs^+$, $Ba^{2+}$ and hydrated $Mg^{2+}$. A more highly hydrated form of zirconium phosphate, theta, variously reported as $Zr(HPO_4)_2 \cdot 8H_2O$ and $Zr(HPO_4)_2 \cdot 6H_2O$, exhibits improved cation exchange properties probably owing to its greater interlayer spacing of 10.4 angstroms. Clearfield et al., J. Inorg. Nuc. Chem., 1964, Vol. 26, pp. 117 to 129, Pergamon Press. The anhydrous phase of zirconium phosphate $Zr(HPO_4)_2$, known as beta zirconium phosphate, and the dihydrate phase, gamma zirconium phosphate $Zr(HPO_4)_2 \cdot 2H_2O$ also exhibit greater interlayer distance than the alpha form with d-spacings of 9.4 and 12.2 angstroms, respectively. Clearfield et al., J. Inorg. Nuc. Chem. 1968, Vol. 30 pp. 2249-2258, Pergamon Press. Like the theta form, these zirconium phosphates of increased interlayer spacing are capable of ion-exchanging bulky cations at a greater rate than the alpha form.

The above zirconium phosphates are normally prepared by addition of a soluble salt of zirconium to a solution of phosphoric acid or a soluble sulfate. In the presence of an excess of the phosphorus derivative, i.e., P:Zr mole ratio >2, a gel is formed which crystallizes when the reactant mixture is maintained at elevated temperature for an extended time, say about 48 hours. Other methods of producing zirconium phosphates are set out in U.S. Pat. Nos. 3,056,647; 3,485,763; 4,025,608 and 4,381,289, all of which are incorporated herein by reference.

Although the resulting materials exhibit a significant ion exchange capability, they suffer from limitations in thermal stability. At temperatures above about 300° C. such materials are subject to losses in sorption and surface acidity.

Zirconium phosphonates have been prepared by reacting organics such as ethylene oxide with the acidic hydroxyl of the layered zirconium phosphate to convert the inorganic acid hydroxyls to bound organic alkanol groups. See, e.g. Yamaka, Inorg. Chem 15, 2811, (1976). Other phosphonates of zirconium including zirconium bis(benzenephosphonate), zirconium bis(hydroxymethanephosphonate) monohydrate and zirconium bis(monoethylphosphonate) have been prepared. Alberti et al., J. Inorg. Nucl. Chem., 40, 1113 (1978). U.S. Pat. No. 4,298,723 to DiGiacomo et al., incorporated herein by reference describes a process for preparing layered materials similar in structure to zirconium phosphates. A source of zirconium such as zirconyl chloride is combined with an organophosphorus acid compound of the formula $((HO)_2OP)_nR$, wherein n is 1 or 2 and R may be an acyclic group, heteroacyclic group containing one or more heteroatoms selected from O, N, and S, a cyclic group, aromatic group, or a heterocyclic group containing one or more heteroatoms selected from O, N and S. The organo groups occupy an average surface area not greater than about 24 square angstroms in each section bounded by four zirconium atoms. The resulting layered material exhibit improved thermal stability over prior art zirconium phosphates.

It has now been found that crystalline zirconium phosphates of high thermal stability and sorption capacity can be prepared by including a bulky organic cations having a molecular weight greater than about 100, 500, 1000 or even 10,000 in a forming mixture which contains a source of zirconium and a source of phosphorus. Crystalline zirconium phosphate compounds of the present invention include those having the composition:

where A is an organic cation having a molecular weight of at least about 100; M' is a cation of valence m; $0<x<4$; $0<y<6$; $0<z<3$; and $0<w<20$. Such materials can be prepared by combining a phosphorus source selected from the group consisting of water-soluble phosphates and phosphoric acid, with a salt of the organic cation, and thereafter combining the resulting mixture with a source of zirconium under crystallization conditions. Cations of onium compounds are particularly useful in preparing zirconium phosphates of the present invention. Onium compounds which may be used include those having the following formula:

wherein R is alkyl of from 1 to 20 carbon atoms, heteroalkyl of from 1 to 20 carbon atoms, aryl, heteroaryl, cycloalkyl of from 3 to 6 carbon atoms, cycloheteroalkyl, of from 3 to 6 carbon atoms, or combinations thereof; p is 1 to 4, preferably 4; M is a quadricoordinate element (e.g., nitrogen, phosphorus, arsenic, antimony or bismuth) or a heteroatom (e.g., N, O, S, Se, P, As, etc.) in an alicyclic, heteroalicyclic or heteroaromatic structure; and X is an anion (e.g., fluoride, chloride bromide, iodide, hydroxide, acetate, sulfate, carboxylate, etc.). When M is a heteroatom in an alicyclic, heteroalicyclic or heteroaromatic structure, the cation $R_pM^+$ may be, as non-limiting examples,

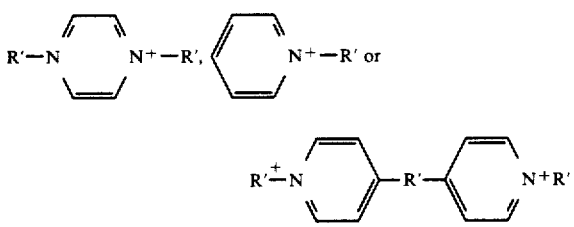

wherein R' is alkyl of from 1 to 20 carbon atoms, heteroalkyl of from 1 to 20 carbon atoms, aryl, heteroaryl, cycloalkyl of from 3 to 6 carbon atoms of cycloheteralkyl of from 3 to 6 carbon atoms.

In particular, tetraalkylammonium compounds have been found to be useful onium compounds in the present invention, e.g., tetrapropylammonium bromide and tetrapropylammonium hydroxide. Compounds containing multiple cationic centers including cationic polymers known as ionomers, may also be used such as those having the formula:

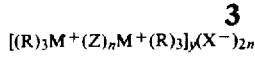

where y > 1 wherein R, M and X are as above defined, Z is a bridging member selected from the group consisting of alkyl of from 1 to 20 carbon atoms, alkenyl of from 2 to 20 carbon atoms, aryl, heteroalkyl of from 1 to 20 carbon atoms, heteralkenyl of from 2 to 20 carbon atoms and heteroaryl, and n is a number of from 1 to about 50. Non-limiting examples of such multiple cationic center containing compounds include:

[$(CH_3)_3As^+(CH_2)_6N^+(CH_3)_3$]($Cl^-$)$_2$,
[$(C_3H_7)_3N^+(CH_2)_{10}N^+(C_3H_7)_3$]($Cl^-$)$_2$,
[$(C_6H_5)_3N^+(C_2H_4)_{16}P^+(C_6H_5)_3$]($OH^-$)$_2$,
[$(C_{18}H_{37})_3P^+(C_2H_2)_3P^+(C_3H_3)$]($Cl^-$)$_2$,
[$(C_2H_5)_3N^+(C_6H_4)N^+(C_2H_5)_3$]($Br^-$)$_2$,
[$(CH_3)_3Sb^+(CH_2)_{10}Sb^+(CH_3)_3$]($Cl^-$)$_2$,
[$(C_6H_5)_3Sb^+(CH_2)_4N^+(CH_3)_3$]($OH^-$)$_2$,
[$(C_2H_3)_3N^+(CH_2)_{50}N^+(C_2H_3)_3$]($OH^-$)$_2$,
[$(C_6H_5)_3P^+(C_2H_2)_6As^+(CH_3)_3$]($Cl^-$)$_2$,
[$(CH_3)_3N^+(CH_2)_6N^+(CH_3)_3$]($Cl^-$)$_2$,
and

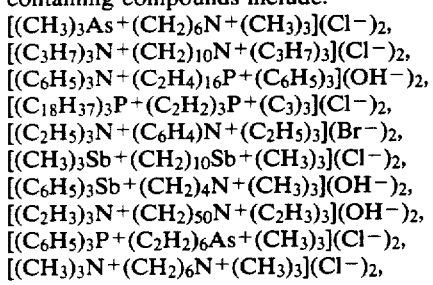

The cation may also be a quaternary phosphorus cation of a salt. The phosphorus-containing salt may be of the type disclosed in U.S. Pat. No. 4,209,449 and 4,336,385 to Mayhew et al. incorporated hereby by reference, and available from Mona Industries, Paterson, N.J. Broadly speaking, such salts are of the formula:

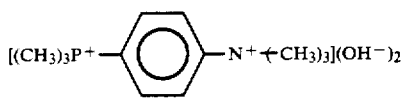

wherein
R is an amidoamine moiety of the formula

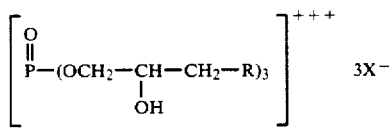

$R^1$ is alkyl, alkenyl, alkoxy, or hydroalkyl of from 5 to 22 carbon atoms each, or aryl or alkary of up to 20 carbon atoms, $R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms;

$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-containing heterocycle;

n is an integer from 2 to 12; and

X is an anion.

In a particularly preferred embodiment, $R_1$ is $C_5$ is $C_{17}$ alkyl, $R_2$ is H, $R_3$ and $R_4$ are methyl and n=3. In another preferred embodiment $R_1$ is $C_{11}$ to $C_{13}$ alkyl and X is Cl.

In another embodiment, R may be

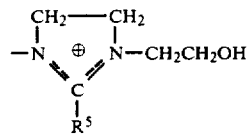

and $R^5$ is $C_5$ to $C_{17}$ alkyl, say, for example, $C_{12}$ alkyl, and X is Cl.

In still another embodiment the phosphorus-containing salt may comprise a zwitterion, for example, materials such as

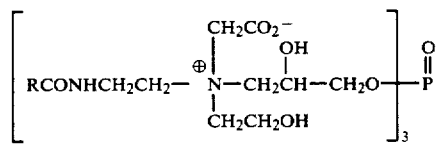

may be included in the forming mixture.

Upon exposure to crystallization conditions a crystalline zirconium phosphate compound is produced, having the composition:

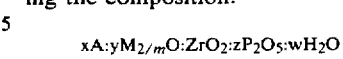

where A is an organic cation of the salt described above; M is a cation of valence m; $0<x<4$; $0<y<6$; $0<z<3$; and $0<w<20$, preferably $0.01<x<2$; $1<y<4$; $0.5<z<2$; and $0<w<10$.

The crystalline material of the present invention exhibits an X-ray diffraction pattern showing the significant lines set out below in Table 1.

TABLE 1

| d-space | 2-theta | I/I$_o$ |
| --- | --- | --- |
| 11.33 + 0.1 | 7.79 | m |
| 3.89 + 0.05 | 22.87 | s |
| 3.29 + 0.03 | 27.05 | vs |
| 3.14 + 0.03 | 28.45 | w-m |
| 2.66 + 0.02 | 33.71 | w |
| 2.63 + 0.02 | 34.10 | w | with I/I$_o$ from 0 to 24%=w (weak), from 25 to 49%=m (medium), from 50 to 74%=s (strong), and from 75 to 100%—vs (very strong).

While not wishing to be bound by theory, it is believed that the surfactant and directing properties of the organic cations, as well as their ability to ion-exchange during synthesis, advantageously affect the gelation of the reactant mixture, the rheology of the obtained gel phase, as well as gel crystallization. The bulkiness of the cations serve to keep the layers far apart during the reaction.

The zirconium phosphate materials of the present invention are made by reacting a source of zirconium and a source of phosphorus in the presence of a bulky organic cation characterized above. Suitable sources of zirconium include zirconium water soluble compounds such as zirconyl chloride, $ZrOCl.8H_2O$. Suitable phosphorus sources include water soluble phosphates or hydrogen phosphates such as $NaH_2PO_4.H_2O$, organophosphorus compounds, phosphorus oxides, and phosphoric acid. Preferably, the bulky organic cationic compound is combined with the phosphorus source, e.g., $NaH_2PO_4.H_2O$ and where necessary, solution is effected by adding an acid solution such as 3N HCl. The resulting mixture can then be refluxed, during which time the source of zirconium, e.g., a 1M $ZrOCl_2.8H_2O$ solution, is gradually added. The P/Zr molar ratio of the resulting forming mixture, exclusive of added organic cation, is greater than 2. Upon addition of zirconium a gel is formed. Crystallization of the gel results from its exposure to refluxing conditions or by autoclaving. Temperatures greater than about 70° C., preferably about 90° C. to 150° C., may be used in effecting crystallization. The pressure may be atmospheric, autogeneous, or any suitable crystallization pressure ranging from about 1 to 30 atm. Depending on the particular conditions employed, crystallization time can range from 1 to 500 hours.

In those situations where an alkali metal-containing phosphorus salt is used as the phosphorus source e.g., a sodium salt of phosphoric acid, some or all ion-exchange sites of the resulting crystalline zirconium phosphate material will be exchanged with alkali metal. In order to convert such material to the proton exchanged form, the as-synthesized crystalline zirconium phosphate is acid washed. Proton-exchange is preferably achieved by contacting the material to be exchanged, with a mixture of hydrochloric and/or phosphoric acid, followed by rinsing with distilled water.

Upon crystallization and any subsequent treatment such as proton-exchange or ammonium exchange, the crystalline material is dried. The drying step may be in any suitable atmosphere, including vacuum or air at temperatures ranging from about 50° to 200° C., say about 120° C.

The dried crystalline zirconium phosphate may then be exposed to thermal treatment, i.e. calcined in an inert gas atmosphere, such as nitrogen or helium, and/or in an oxygen-containing atmosphere, e.g., air. Suitable calcining temperatures can range from about 200° to 600° C., say about e.g., 250° C. or 500° C. Such treatment results in removal of at least some of the organic cation present in the structure of the zirconium phosphate.

The calcined materials exhibit thermal stability at temperatures of 400° C. or even higher. In addition, these materials possess strong acid sites and enhanced surface acidity. Accordingly, the zirconium phosphate materials of the present invention are significantly better than prior art zirconium phosphates which exhibit poor thermal stability and reduction in surface acidity when exposed to temperature above 300° C. Thus, the present invention may be used to prepare zirconium phosphates which may be used as ion exchangers or catalysts under a wide variety of operating conditions and temperatures. For example, they may be used in their acid form for acid-catalyzed reactions. Ion-exchange of the zirconium phosphate with metal ions yields a catalyst suitable for oxidation or base-catalyzed reactions. The zirconium phosphates of the present invention may be employed in converting organic compounds by contacting said compounds with the zirconium phosphates at conversion conditions. In addition, the products of the invention may be used as a catalyst binder owing to their thermal stability.

The following examples further describe the invention but are not to be considered limiting in any way.

EXAMPLES 1-10

Preparation of Zirconium Phosphates

A series of zirconium phosphate compounds, ZP-1 through ZP-10, corresponding to the product of Examples 1 through 10 were prepared in accordance with Table 2. ZP-1 and ZP-9 were conventionally prepared in the absence of bulky organic ions in the forming mixture. The remaining materials were prepared in the presence of organic ions derived from quaternary ammonium compounds such as tetrapropylammonium bromide (TPABr), tetrapropylammonium hydroxide (TPAOH) and Monaquat PT-Z, a compound-having the formula:

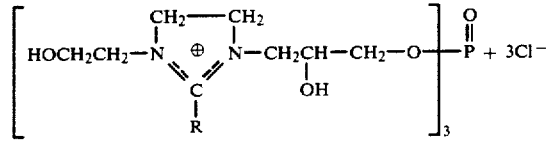

TABLE 2

| Designation | SYNTHESIS AND CHARACTERISTICS OF ZIRCONIUM PHOSPHATES | | | | | | | | | |
|---|---|---|---|---|---|---|---|---|---|---|
| | ZP-1 | ZP-2 | ZP-3 | ZP-4 | ZP-5 | ZP-6 | ZP-7 | ZP-8 | ZP-9 | ZP-10 |
| Reaction Mixture (g) | | | | | | | | | | |
| Na—phosphate | 68 | 68 | 68 | 68 | 68 | 68 | 68 | 68 | 68 | 68 |
| Zr—oxychloride | 8 | 8 | 8 | 8 | 8 | 8 | 8 | 8 | 8 | 8 |
| HCl | 5.5 | 5.5 | 5.5 | 5.5 | 5.5 | 5.5 | 5.5 | 5.5 | 5.5 | 5.5 |
| Water | 75 | 75 | 75 | 75 | 130 | 75 | 100 | 75 | 75 | 75 |
| Organic cmpd. | — | A | A | A | B | A | A | A | — | C |
| A = TPABr | | | | | | | | | | |
| B = TPAOH | | | | | | | | | | |
| C = Monaquat PT-Z | | | | | | | | | | |
| Organic (g) | — | 132 | 40 | 40 | 19 | 40 | 40 | 40 | — | 10 |
| Temperature (°C.) | 95 | 95 | 95 | 135 | 95 | 135 | 135 | 135 | 135 | 135 |
| Time (hrs) | 25 | 25 | 25 | 25 | 25 | 48 | 25 | 168 | 25 | 25 |
| Product composition (wt. %) | | | | | | | | | | |
| C | — | 0.1 | 0.1 | 2.3 | 4.0 | 0.3 | 3.6 | 4.4 | — | 14.9 |
| N | — | — | — | 0.1 | 0.2 | — | — | 0.2 | — | 0.2 |
| Na | 6.0 | 3.8 | 4.3 | 6.1 | 9.9 | 5.3 | 0.5 | 14.2 | 8.3 | 2.8 |
| Cl | — | n.t. | n.t. | n.t. | 2.5 | 0.1 | — | 2.3 | 1.6 | 1.3 |
| Zr | 29.1 | 29.6 | 29.9 | 28.8 | 20.8 | 27.2 | 26.9 | 18.3 | 22.6 | 20.3 |
| P | 20.5 | 20.9 | 20.3 | 19.7 | 20.6 | 19.7 | 19.9 | 19.8 | 21.9 | 17.2 |

TABLE 2-continued

| SYNTHESIS AND CHARACTERISTICS OF ZIRCONIUM PHOSPHATES | | | | | | | | | | |
|---|---|---|---|---|---|---|---|---|---|---|
| Designation | ZP-1 | ZP-2 | ZP-3 | ZP-4 | ZP-5 | ZP-6 | ZP-7 | ZP-8 | ZP-9 | ZP-10 |
| Product molar composition | | | | | | | | | | |
| PZr | 2.06 | 2.07 | 1.99 | 2.01 | 2.91 | 2.12 | 2.17 | 3.17 | 2.83 | 2.49 |
| Na/P | 0.39 | 0.25 | 0.29 | 0.42 | 0.65 | 0.36 | 0.03 | 0.97 | 0.51 | 0.22 |
| Adsorption (n-hexane, wt. %, at 30° C.) | | | | | | | | | | |
| Calc. 250 C | 1.20 | 1.80 | — | 1.72 | 0.73 | 2.10 | — | 0.95 | 0.12 | 1.80 |
| Calc. 500 C | 1.20 | 1.60 | 0.90 | 1.77 | 0.33 | 2.30 | — | 1.12 | 0.00 | 2.10 |

The materials of the present invention were prepared as follows:

The organic cation compound and 68 g of NaH$_2$PO$_4$·H$_2$O were dissolved in 50 ml of 3N HCl at reflux. 25.0 ml of 1M ZrOCl$_2$.8H$_2$O was then added dropwise over a period of about 30 mins. A gel resulted which was crystallized by autoclaving at 135° C. or refluxing at about 95° C. for about 25 to 170 hours. The crystallized sodium-exchanged product was then filtered and washed. Sodium ion was proton-exchanged by acid washing in 2N HCl and 0.2M H$_3$PO$_4$ followed by rinsing with distilled water. The acid forms of the zirconium phosphate was then dried in an oven at 120° C.

EXAMPLE 11

Thermal Stability of Zirconium Phosphate

X-ray diffraction patterns of ZP-4, a zirconium phosphate prepared from a forming mixture which contains tetrapropylammonium bromide were obtained by standard techniques for as-synthesized ZP-4, ZP-4 calcined at 350° C., and ZP-4 calcined at 500° C. The X-ray diffractograms were substantially the same except for minor shifts in interplanar spacing and variation in relative intensity. Thus, it is seen that ZP-4 is thermally stable even at temperatures of 500° C.

EXAMPLE 12

X-Ray Diffraction Pattern of Treated ZP-4

ZP-4 was treated by NaOH according to the following procedure:
(1) Add 1.0 g ZP-4 (as synthesized) to 130 mg NaOH in 200 ml water.
(2) Stir for 3 hours at ambient temperature.
(3) Filter, without washing, and dry at 100° C.

Another sample of ZP-4 was treated with dimethylsilane by heating 2.0 g ZP-4 to 250° C. (5°/min), while flowing dimethylsilane continuously through the reactor at 60 cc/min.

X-ray diffraction patterns of the samples were then obtained by conventional methods. A comparison of the two patterns showed that the crystalline structure was essentially maintained, as minor shifts only occurred in interplanar spacings. Furthemore, the uptake of dimethylsilane, a material which is relatively inert to weakly acidic conditions, indicates the presence of very strong acid sites in the partially protonated form of ZP-4.

EXAMPLE 13

Reproducibility of ZP-4 Synthesis

Another batch of ZP-4 was prepared according to the procedure of Example 4. A comparison of X-ray diffraction patterns of the materials of Examples 4 and 13, indicated the reproducibility of the synthesis product.

What is claimed is:

1. A method for preparing in an aqueous reaction mixture crystalline zirconium phosphate compounds having the composition:

$$xA:yM'_{2/m}O:ZrO_2:zP_2O_5:wH_2O$$

where A is an organic cation having a molecular weight of at least about 100; M' is a cation of valence m; $0<x<4$; $0<y<6$; $0<z<3$; and $0<w<20$, wherein a phosphorus source selected from the group consisting of water-soluble phosphates and phosphoric acid is combined with a salt of said organic cation, and thereafter combined with a source of zirconium under crystallization conditions.

2. The method of claim 1 wherein said phosphorus source comprises NaH$_2$PO$_4$.H$_2$O; said source of zirconium is ZrOCl$_2$.8H$_2$O; $0.01<x<2$; $1<y<4$; $0.5<z<2$; and $0<w<10$.

3. The method of claim 1 wherein said organic cation is a cation of the compound $$R_4M^+X^-$$

wherein R is selected from the group consisting of alkyls of from 1 to 20 carbon atoms, heteroalkyls of from 1 to 20 carbon atoms, aryls, heteroaryls, cycloalkyls of from 3 to 6 carbon atoms, cycloheteroalkyls, of from 3 to 6 carbon atoms; M is a quadricoordinate element selected from the group consisting of nitrogen, phosphorus, arsenic, and antimony and X is an anion selected from the group consisting of fluoride, chloride, bromide, iodide, hydroxide, acetate, sulfate, and carboxylate.

4. The method of claim 3 wherein R is an alkyl of from 1 to 20 carbon atoms and M is nitrogen.

5. The method of claim 4 wherein R is propyl.

6. The method of claim 1 wherein said organic cation is a cation of the salt $$R_pM^+X^-$$

wherein R is selected from the group consisting of alkyls of from 1 to 20 carbon atoms, heteroalkyls of from 1 to 20 carbon atoms, aryls, heteroaryls, cycloalkyls of from 3 to 6 carbon atoms, cycloheteroalkyls, of from 3 to 6 carbon atoms; p is 1 to 4; M is a heteroatom selected from the group consisting of nitrogen, oxygen, sulfur, selenium, phosphorus and arsenic in a structure selected from the group consisting of alicyclics, heteroalkicyclics, and heteroaromatics; and X is an anion selected from the group consisting of fluoride, chloride, bromide, iodide, hydroxide, acetate, sulfate, and carboxylate.

7. The method of claim 6 wherein said organic cation is selected from the group consisting of

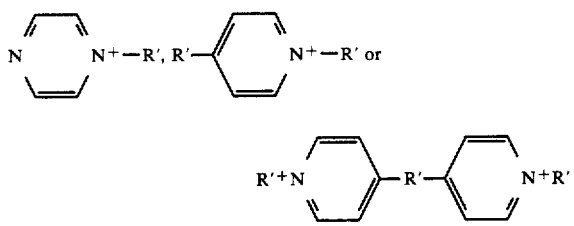

wherein R' is selected from the group consisting of alkyl of from 1 to 20 carbon atoms, heteroalkyl of from 1 to 20 carbon atoms, aryl, heteroaryl, cycloalkyl of from 3 to 6 carbon atoms and cycloheteroalkyl of from 3 to 6 carbon atoms.

8. The method of claim 1 wherein said salt is of the formula:

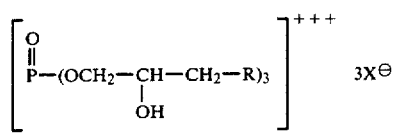

wherein
R is an amidoamine moiety of the formula

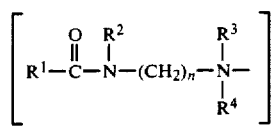

wherein
- $R^1$ is selected from the group consisting of alkyl, alkenyl, alkoxy, and hydroxyalkyl of from 5 to 22 carbon atoms each; and aryl or alkaryl of up to 20 carbon atoms,
- $R^2$ is selected from the group consisting of hydrogen, alkyl, hydroxyalkyl or alkenyl of up to 6 carbon atoms each; cycloalkyl of up to 6 carbon atoms and polyoxyalkylene of up to 10 carbon atoms;
- $R^3$ and $R^4$, which may be the same or different, are selected from the group consisting of alkyl, hydroxyalkyl, carboxyalkyl of up to 6 carbon atoms in each alkyl moiety; polyoxyalkylene of up to 10 carbon atoms; and $R^3$ and $R^4$ taken together with the nitrogen to which they are attached as an N-heterocycle;
- n is an integer from 2 to 12; and
- X is an anion.

9. The method of claim 8 wherein $R_1$ is $C_5$ to $C_{17}$ alkyl, $R_2$ is H, $R_3$ and $R_4$ are methyl and n=3.

10. The method of claim 9 wherein $R_1$ is $C_{11}$ to $C_{13}$ alkyl and X is Cl.

11. The method of claim 6 wherein R is

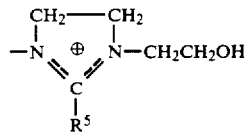

and $R^5$ is $C_5$ to $C_{17}$ alkyl.

12. The method of claim 11 wherein $R^5$ is $C_{12}$ alkyl and X is Cl.

13. The method of claim 12 wherein $0.01 < x < 1$; $1 < y < 4$; $0.5 < z < 2$; and $0 < w < 10$.

14. The method of claim 1 wherein said crystallization conditions include crystallization under reflux.

15. The method of claim 1 wherein said crystallization conditions comprise temperatures greater than about 100° C.

16. The method of claim 14 wherein the crystallized product is proton-exchanged by acid washing.

17. The method of claim 16 wherein said acid washing is effected by contacting the crystallized product with about 2N HCl and 0.2M $H_3PO_4$.

18. The method of claim 15 wherein the crystallized product is proton-exchanged by acid washing.

19. The method of claim 18 wherein said acid washing is effected by contacting the crystallized product with 2N HCl and 2M $H_3PO_4$.

20. The method of claim 16 wherein the proton-exchanged product is dried at about 50° to 200° C.

21. The method of claim 18 wherein the proton-exchanged product is dried at about 50° to 200° C.

22. A crystalline zirconium phosphate compound having the composition:

$$xA:yM'_{2/m}O:ZrO_2:zP_2O_5:wH_2O$$

where A is an organic cation; M' is a cation of valence m; 0×4; 0y6; 0z3; 0w20; and having the significant X-ray diffraction lines of Table 1 of the specification.

23. The compound of claim 22 wherein said organic cation is a cation of the salt $$R_4M^+X^-$$

wherein R is selected from the group consisting of alkyls of from 1 to 20 carbon atoms, heteroalkyls of from 1 to 20 carbon atoms, aryls, heteroaryls, cycloalkyls of from 3 to 6 carbon atoms, cycloheteroalkyls, of from 3 to 6 carbon atoms; M is a quadricoordinate element selected from the group consisting of nitrogen, phosphorus, arsenic, and antimony and X is an anion selected from the group consisting of fluoride, chloride, bromide, iodide, hydroxide, acetate, sulfate, and carboxylate.

24. The compound of claim 23 wherein R is an alkyl of from 1 to 20 carbon atoms and M is nitrogen.

25. The compound of claim 24 wherein R is propyl.

26. The compound of claim 22 wherein said organic cation is a cation of the salt PS $$R_4M^+X^-$$

wherein R is selected from the group consisting of alkyls of from 1 to 20 carbon atoms, heteroalkyls of from 1 to 20 carbon atoms, aryls, heteroaryls, cycloalkyls of from 3 to 6 carbon atoms, and cycloheteroalkyls of from 3 to 6 carbon atoms; M is a heteroatom selected from the group consisting of nitrogen, oxygen, sulfur, selenium, phoshorus and arsenic in a structure selected from the group consisting of alicyclics, heteroalicyclics, and heteroaromatics; and X is an anion selected from the group consisting of fluoride, chloride, bromide, iodide, hydroxide, acetate, sulfate, and carboxylate.

27. The compound of claim 26 wherein M is selected from the group consisting of

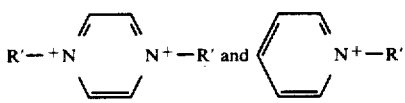

wherein R' is selected from the group consisting of alkyl of from 1 to 20 carbon atoms, heteroalkyl of from 1 to 20 carbon atoms, aryl, heteroaryl, cycloalkyl of from 3 to 6 carbon atoms and cycloheteroalkyl of from 3 to 6 carbon atoms.

28. The compound of claim 22 wherein A is an organic phosphate quaternary cation.

29. The compound of claim 22 wherein A is

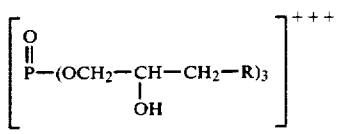

wherein
R is an amidoamine moiety of the formula

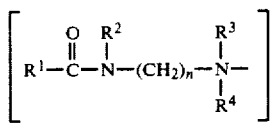

wherein
$R^1$ is selected from the group consisting of alkyl, alkenyl, alkoxy, hydroxyalkyl, of from 5 to 22 carbon atoms each, and aryl or alkaryl of up to 20 carbon atoms,
$R^2$ is selected from the group consisting of hydrogen, alkyl, hydroxyalkyl, alkenyl, of up to 6 carbon atoms each; cycloalkyl of up to 6 carbon atoms; and polyoxyalkylene of up to 10 carbon atoms;
$R^3$ and $R^4$, which may be the same or different, are selected from the group consisting of alkyl, hydroxyalkyl, carboxyalkyl, of up to 6 carbon atoms in each alkyl moiety; polyoxyalkylene of up to 10 carbon atoms; and $R^3$ and $R^4$ taken together with the nitrogen to which they are attached, as an N-heterocycle;
and n is an integer from 2 to 12;

30. The compound of claim 29 wherein $R_1$ is $C_5$ to $C_{17}$ alkyl, $R_2$ is H, $R_3$ and $R_4$ are methyl and n=3.

31. The compound of claim 30 wherein $R_1$ is $C_{11}$ to $C_{13}$ alkyl.

32. The compound of claim 29 wherein R is

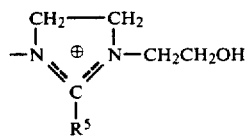

and $R^5$ is $C_5$ to $C_{17}$ alkyl.

33. The compound of claim 32 wherein $R^5$ is $C_{12}$ alkyl.

34. The compound of claim 33 wherein $0.01 < x < 1$; $1 < y < 4$; $0.5 < z < 2$; and $0 < w < 10$.

35. A crystalline zirconium phosphate resulting from thermal treatment of the compound of claim 22.

36. A crystalline zirconium phosphate resulting from thermal treatment of the compound of claim 23.

37. A crystalline zirconium phosphate resulting from thermal treatment of the compound of claim 24.

38. A crystalline zirconium phosphate resulting from thermal treatment of the compound of claim 25.

39. A crystalline zirconium phosphate resulting from thermal treatment of the compound of claim 26.

40. A crystalline zirconium phosphate resulting from thermal treatment of the compound of claim 29.

41. A crystalline zirconium phosphate resulting from thermal treatment of the compound of claim 32.

42. A crystalline zirconium phosphate resulting from thermal treatment of the compound of claim 33.

* * * * *

UNITED STATES PATENT AND TRADEMARK OFFICE
CERTIFICATE OF CORRECTION

PATENT NO. : 4,695,642

DATED : September 22, 1987

INVENTOR(S) : E. G. Derouane et al

It is certified that error appears in the above—identified patent and that said Letters Patent is hereby corrected as shown below:

Col. 3, line 16, "$[(C_{18}H_{37})_3P^+(C_2H_2)_3P^+(C_3)_3](Cl^-)_2$" should read
--$[(C_{18}H_{37})_3P^+(C_2H_2)_3P^+(CH_3)_3](Cl^-)_2$--

Col. 4, line 5   "$C_5$ is $C_{17}$" should read --$C_5$ to $C_{17}$--

Col. 10, line 31   "$Oy6$" should read --O  y  6-- and
"$ow20$" should read --O  w  20--

Signed and Sealed this

Fourteenth Day of June, 1988

Attest:

DONALD J. QUIGG

Attesting Officer        Commissioner of Patents and Trademarks